United States Patent [19]

Bourzat et al.

[11] Patent Number: 4,898,871

[45] Date of Patent: Feb. 6, 1990

[54] PYRROLE DERIVATIVES AND PHARMACEUTICAL COMPOSITIONS WHICH CONTAIN THEM AS HYPNOTICS AND ANTICONVULSANTS

[75] Inventors: Jean-Dominique Bourzat, Paris; Marc Capet, Thiais; Claude Cotrel, Paris; Richard Labaudiniere, Vitry S/Seine; Philippe Pitchen, Marolles-enBrie; Gerard Roussel, Soisy S/Seine, all of France

[73] Assignee: Rhone-Poulenc Sante, Courbevoie, France

[21] Appl. No.: 126,352

[22] Filed: Nov. 30, 1987

[30] Foreign Application Priority Data

Dec. 2, 1986 [FR] France .................. 86 16794

[51] Int. Cl.$^4$ ............... A61K 31/435; C07D 471/02; C07D 211/00
[52] U.S. Cl. ................... 514/300; 546/122; 546/15; 514/278
[58] Field of Search ........... 546/122, 15; 514/278, 514/300

[56] References Cited

U.S. PATENT DOCUMENTS

| 4,000,306 | 12/1976 | Cotrel et al. | 514/421 |
| 4,001,271 | 1/1977 | Cotrel et al. | 546/272 |
| 4,786,642 | 11/1988 | Teulon | 546/122 |

FOREIGN PATENT DOCUMENTS

| 2217000 | 6/1974 | France | 546/122 |

*Primary Examiner*—Mary C. Lee
*Assistant Examiner*—Robert C. Whittenbaugh
*Attorney, Agent, or Firm*—Stevens, Davis, Miller & Mosher

[57] ABSTRACT

Pyrrole derivatives of formula

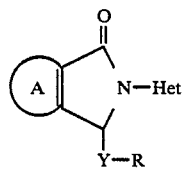

in which A forms with the pyrrole ring an isoindoline, 6,7-dihydro-5H-pyrrolo-[3,4-b]pyrazine, 2,3,6,7-tetrahydro-5H-[1,4]-oxathiino-[2,3-c]pyrrole or 2,3,6,7-tetrahydro-5H-[1,4]dithiino-[2,3-c]pyrrole ring-system, Y+0, S or NH, Het=naphthyridinyl or quinolyl which are unsubstituted or substituted with halogen, (1 to 4 C) alkyl, (1 to 4 C) alkyloxy, (1 to 4 C) alkylthio, CN or $CF_3$ and R=(3 to 10 C) alkenyl or alkyl which is unsubstituted or substituted with alkyloxy, alkylthio, cycloalkyl, alkylcarbonyl, cycloalkylcarbonyl or cycloalkylcarbamoyl in which the cycloalkyl portions contain 3 to 6 C, $NH_2$, alkylamino, dialkylamino, alkylcarbonylamino, 1- or 2-piperazinyl, piperidyl, piperidino, morpholino, 1-azetidinyl, pyrrolidinyl, carbamoyl, alkylcarbamoyl, dialkylcarbamoyl, (1-piperazinyl)carbonyl, piperidinocarbonyl, piperidylcarbonyl, (1-pyrrolidinyl)carbonyl, morpholinocarbonyl, aminoalkylcarbamoyl, alkylaminoalkylcarbamoyl, dialkylaminoalkylcarbamoyl, alkyloxyalkylcarbamoyl, phenyl, pyridyl, or 1-imidazolyl, or R=2- or 3-pyrrolidinyl, or 1-imidazolyl, or 2-, 3- or 4-piperidyl, the aforesaid piperazinyl, piperidino, piperidyl, pyrrolidinyl, and azetidinyl radicals being unsubstituted or substituted at any position by alkyl, OH, alkylcarbonyl, benzyl, or hydroxyalkyl, or can form (i) a lactam group with the nitrogen atom of the ring or (ii) a 2-spirodioxolane residue with a carbon of the ring, and the said alkyl radicals containing 1 to 10 C except where specifically stated, are useful as anxiolytics.

11 Claims, No Drawings

PYRROLE DERIVATIVES AND PHARMACEUTICAL COMPOSITIONS WHICH CONTAIN THEM AS HYPNOTICS AND ANTICONVULSANTS

The present invention provides new pyrrole derivatives of the formula:

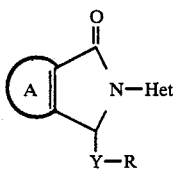
(I)

in which A forms with the pyrrole ring an isoindoline, 6,7-dihydro-5H-pyrrolo[3,4-b]pyrazine, 2,3,6,7-tetrahydro-5H-[1,4]oxathiino[2,3-c]pyrrole or 2,3,6,7-tetrahydro-5H-[1,4]dithiino[2,3-c]pyrrole ring-system, Y denotes an oxygen or sulphur atom or an imino radical, Het denotes a naphthyridinyl or quinolyl radical which is unsubstituted or substituted by halogen, (1 to 4 C) alkyl, (1 to 4 C) alkyloxy, (1 to 4 C) alkylthio, cyano or trifluoromethyl and R denotes straight- or branched-chain alkenyl of 3 to 10 carbon atoms or alkyl which is unsubstituted or substituted by alkyloxy, alkylthio, cycloalkyl, alkylcarbonyl, cycloalkylcarbonyl in which the cycloalkyl has 3 to 6 carbon atoms, cycloalkylcarbamoyl in which the cycloalkyl has 3 to 6 carbon atoms, amino, alkylamino, dialkylamino, alkylcarbonylamino, 1- or 2-piperazinyl, piperidyl, piperidino, morpholino, 1-azetidinyl, pyrrolidinyl, carbamoyl, alkylcarbamoyl, dialkylcarbamoyl, (1-piperazinyl)carbonyl, piperidinocarbonyl, piperidylcarbonyl, (1-pyrrolidinyl)carbonyl, morpholinocarbonyl, aminoalkylcarbamoyl, alkylaminoalkylcarbamoyl, dialkylaminoalkylcarbamoyl, alkyloxyalkylcarbamoyl, phenyl, pyridyl or 1-imidazolyl, or R denotes 2- or 3-pyrrolidinyl or 2-, 3- or 4-piperidyl, the aforesaid alkyl radicals being straight- or branched-chain radicals and containing, except where specifically stated, 1 to 10 carbon atoms each, and the said piperazinyl, piperidino, piperidyl, pyrrolidinyl and azetidinyl radicals being unsubstituted or substituted at any position by alkyl, hydroxy, alkylcarbonyl, benzyl or hydroxyalkyl, or can form (i) a lactam group with the nitrogen atom of the ring or (ii) a 2-spirodioxolane residue with a carbon of the ring, as well as, where they exist, their pharmaceutically acceptable salts and their optical isomers.

According to a feature of the invention, the pyrrole derivatives of formula (I) in which Y denotes an oxygen or sulphur atom, Het is as defined above with the exception of denoting a naphthyridinyl radical substituted by alkyloxy or alkylthio, and the other symbols are defined as above, are prepared by the action of a compound of general formula:

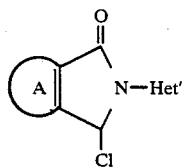
(II)

in which Het' has the definition of Het given above with the exception of a naphthyridinyl radical substituted by alkyloxy or alkylthio, and A is as defined above, on a compound of general formula:

$$R-Y'-H \quad (III)$$

in which Y' denotes an oxygen or sulphur atom and R is as defined above.

The reaction is generally performed in an organic solvent such as an ether, e.g. tetrahydrofuran, or such as dimethylformamide, in the presence of a base such as an alkali metal hydride, e.g. sodium hydride, at a temperature of between $-5°$ and $+25°$ C.

The compounds of formula (II) may be prepared by chlorination of compounds of general formula:

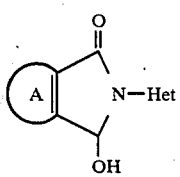
(IV)

in which A and Het are defined as above.

The reaction is generally performed in the presence of a chlorinating agent such as sulphinyl chloride or phosphorus oxychloride, in the presence of catalytic amounts of dimethylformamide, at a temperature between 20° C. and the refluxing temperature of the reaction mixture, or any other agent known to those skilled in the art which enables a hydroxy radical to be converted to a chloro radical without affecting the remainder of the molecule.

The products of general formula (IV) may be prepared by application or adaptation of the methods described in Belgian Pat. Nos. 835,325, 815,019 or 808,152.

According to a further feature of the invention, the pyrrole derivatives of general formula (I) are also prepared by the action of a product of general formula (IV) as defined above on a derivative of formula:

$$RX \quad (V)$$

in which R is as defined above and X denotes a halogen atom or a reactive ester residue such as mesyloxy or tosyloxy.

The reaction is generally performed in an organic solvent such as dimethylformamide or an aromatic hydrocarbon such as toluene or a mixture of these solvents, in the presence of an alkali metal hydride, e.g. sodium hydride, at a temperature of between 0° and 80° C.

According to another feature of the invention, the pyrrole derivatives of formula (I) in which Y denotes a sulphur atom and the other symbols are as defined above are prepared by the action of a compound of general formula:

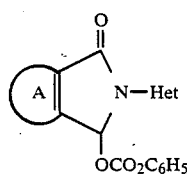
(VI)

in which A and Het are as defined above (or by the action of an equivalent carbonate) on a mercaptan of general formula:

R—SH (VII)

in which R is as defined above.

The reaction is generally performed in an organic solvent such as acetonitrile, at a temperature between 25° C. and the refluxing temperature of the reaction mixture.

According to yet another feature of the invention, the pyrrole derivatives of general formula (I) in which Y denotes an imino radical and the other symbols are defined as above are prepared by the action of a compound of formula (II) or (IV) as defined above on an amine of general formula:

R—NH$_2$ (VIII)

in which R is as defined above.

The reaction is generally performed by simply heating to a temperature between 25° C. and the refluxing temperature of the reaction mixture, in an organic solvent such as tetrahydrofuran or dimethylformamide.

According to yet another feature of the invention, the pyrrole derivatives of formula (1) in which Y denotes an oxygen atom, R denotes a methyl radical substituted with a carbamoyl, alkylcarbamoyl, dialkylcarbamoyl, (1-piperazinyl)carbonyl, piperidinocarbonyl, morpholinocarbonyl, aminoalkylcarbamoyl, alkylaminoalkylcarbamoyl, dialkylaminoalkylcarbamoyl or alkyloxyalkylcarbamoyl radical and the other symbols are defined as above are prepared by the action of a compound of general formula:

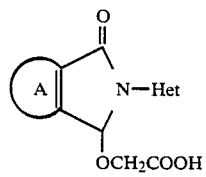
(IX)

or an activated form of this acid, in which A and Het are defined as above, on a compound of general formula:

(X)

in which R$_1$ and R$_2$ denote a hydrogen atom or an alkyl radical, or alternatively R$_1$ denotes a hydrogen atom and R$_2$ denotes an alkyl, aminoalkyl, alkylaminoalkyl, dialkylaminoalkyl or alkyloxyalkyl radical, or alternatively R$_1$ and R$_2$ form, with the nitrogen atom to which they are linked, a piperazine, piperidine or morpholine ring, it being possible for these rings to be substituted as stated above, with the exception of the option in which these rings form a lactam group.

The reaction is generally performed in an organic solvent such as dimethylformamide, in the presence of carbonyldiimidazole, or any other activated form of the acid, at a temperature of between 20° and 80° C.

The acid of general formula (IX) may be obtained by the action of an alkylbromoacetate of general formula:

Br—CH$_2$COOR$_3$ (XI)

in which R$_3$ denotes a straight- or branched-chain alkyl radical containing 1 to 4 carbon atoms, on a product of general formula (IV) in which A and Het are defined as above, followed by a hydrolysis of the corresponding ester.

The condensation of the product of general formula (XI) with the product of general formula (IV) is generally performed in an organic solvent such as dimethylformamide, in the presence of a base such as an alkali metal hydride, e.g. sodium hydride, at a temperature of between −5° and +25° C.

The hydrolysis of the corresponding ester is performed by any known method for converting an ester to an acid. In particular, when R$_3$ denotes a tert-butyl radical, it is advantageous to perform the hydrolysis by means of trifluoroacetic acid at a temperature in the region of 20° C.

According to the invention, the products of general formula (I) in which Y denotes an oxygen atom and the other symbols are defined as above may also be prepared by the action of a product of general formula:

ROMe (XII)

in which R is defined as above and Me denotes an alkali metal such as sodium or potassium, on a product of general formula:

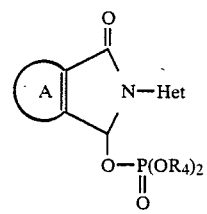
(XIII)

in which R$_4$ denotes a straight- or branched-chain alkyl radical containing 1 to 4 carbon atoms or a phenyl radical, and A and Het are defined as above.

The reaction is generally performed in an organic solvent such as dimethylformamide, at a temperature of between 0° C. and 25° C.

The products of general formula (XIII) may be prepared by the action of a product of general formula:

Cl—P(OR$_4$)$_2$ (XIV)
‖
O in which R$_4$ denotes a straight- or branched-chain radical containing 1 to 4 carbon atoms or a phenyl radical, on a product of general formula (IV) in which A and Het are defined as above.

The reaction is generally performed in an organic solvent such as dimethylformamide, in the presence of a base such as an alkali metal hydride, e.g. sodium hydride, at a temperature of between −5° and +25° C.

It is not necessary to isolate the product of general formula (XIII) in order to carry out the process according to the invention. It is sufficient to perform the condensation of the products of general formulae (XIV) and (IV) as has just been stated, and then to add the product of general formula (XII) to the reaction mixture.

According to the invention, the products of general formula (I) in which Y denotes an imino radical and the other symbols are defined as above may also be prepared by the action of a derivative of general formula (V) defined as above on a product of general formula:

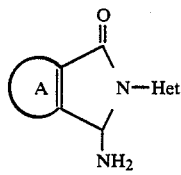

in which A and Het are defined as above.

The reaction is generally performed in a chlorinated solvent such as chloroform, in the presence of an acceptor for acid such as a base, e.g. triethylamine or an alkali metal carbonate or bicarbonate, at a temperature between 0° C. and the refluxing temperature of the reaction mixture.

The products of general formula (XV) may be prepared by the action of ammonia on a product of general formula (II) in which A is defined as above and Het' has the definition given above for Het.

As may be realized by those versed in the art, some radicals falling within the definition of the symbol R are incompatible with the reactants employed during the reactions, and must be protected prior to carrying out the processes, or some phases of the processes, described above. This is the case, in particular, when the radical R contains primary or secondary amino groups or hydroxyl groups which are capable of giving rise to side reactions in the presence of metal hydrides or halogenating reagents. In this case, the said groups must be protected by any method known to those versed in the art, and then unblocked after reaction.

The new products of general formula (I) may be purified by the usual known methods, e.g. by crystallization, chromatography or successive extractions in acidic and basic medium.

The new products of general formula (I) may be converted to an addition salt with acids, by the action of an acid in water or in an organic solvent such as an alcohol, a ketone, an ether or a chlorinated solvent. The salt formed precipitates, where appropriate after concentration of its solution; it is separated by filtration or after settling has occurred.

The products of general formula (I) possess especially advantageous pharmacological properties, which reveal an anxiolytic, hypnotic, anticonvulsant, antiepileptic and muscle relaxant activity. Thus, they show appreciable affinity in vitro for benzodiazepine receptor sites at concentrations which values are between 0.4 and 200 nM according to the technique described by J. C. BLANCHARD and L. JULOU, J. of Neurochemistry, 40, 601 (1983) modelled on the work of SQUIRES and BRAESTRUP, Nature, 266, 732 (1977).

In animals (mice), they have been shown to be active, at doses which are generally of between 3 and 200 mg/kg orally, with respect to pentetrazole-induced convulsions according to a technique closely allied to that of EVERETT and RICHARDS, J. Pharmacol., 81, 402 (1944).

The new products of general formula (I) and their salts possess, in addition, low toxicity. Their oral $LD_{50}$ is generally greater than 300 mg/kg in mice.

For medicinal use, the new products of general formula (I) may be employed as they are or in the state of pharmaceutically acceptable salts, i.e. salts which are non-toxic at the doses at which they are used.

As examples of pharmaceutically acceptable salts, there may be mentioned the addition salts with inorganic acids, such as hydrochlorides, sulphates, nitrates and phosphates, or with organic acids, such as acetates, propionates, succinates, benzoates, fumarates, maleates, methanesulphonates, isethionates, theophyllineacetates, salicylates, phenolphthalinates and methylenebis($\beta$-oxynaphthoates), or substitution derivatives of these compounds.

Of special value are the products of general formula (I) in which A forms with the pyrrole ring an isoindoline, 6,7-dihydro-5H-pyrrolo[3,4-b]pyrazine or 2,3,6,7-tetrahydro-5H-[1,4]dithiino[2,3-c]pyrrole ring-system, Y denotes an oxygen or sulphur atom or an imino radical, Het denotes a 1,8-naphthyridin-2-yl radical substituted with a halogen atom or a (1 to 4 C) alkyl or (1 to 4 C) alkyloxy radical and R denotes a straight- or branched-chain alkenyl radical containing 3 to 10 carbon atoms or an alkyl radical which is unsubstituted or substituted with an alkyloxy, cycloalkyl or alkylcarbonyl radical, with a cycloalkylcarbonyl or cycloalkylcarbamoyl radical in which the cycloalkyl portions contain 3 to 6 carbon atoms, or with a dialkylamino, alkylcarbonylamino, 1-piperazinyl, piperidyl, piperidino, alkylcarbamoyl, dialkylcarbamoyl, (1-piperazinyl)carbonyl, piperidonocarbonyl, morpholinocarbonyl, dialkylaminoalkylcarbamoyl, alkyloxyalkylcarbamoyl, pyridyl or 1-imidazolyl radical, or alternatively R denotes a 2-, 3- or 4-piperidyl radical, on the understanding that the alkyl radicals contain, except where specifically stated, 1 to 6 straight- or branched-chain carbon atoms, and that the and piperidyl, piperidino, piperidyl, radicals can be unsubstituted or substituted at any position with one or more alkyl, hydroxy or alkylcarbonyl radicals, or can alternatively form (i) a lactam group with the nitrogen atom of the ring, or (ii) a 2-spirodioxolane residue with a carbon of the ring.

Of more special value are the products of general formula (I) in which A forms an isoindoline ringsystem with the pyrrole ring, Y denotes an oxygen atom, Het denotes a 1,8-naphthyridin-2-yl radical substituted with a halogen atom or a (1 to 4 C) alkyl or (1 to 4 C) alkyloxy radical and R denotes an alkyl radical which is unsubstituted or substituted with an alkyloxy, cycloalkyl or alkylcarbonyl radical or with a cycloalkylcarbamoyl radical in which the cycloalkyl portions contain 3 to 6 carbon atoms, or with a dialkylamino, piperidyl, piperidino, alkylcarbamoyl, dialkylcarbamoyl, (1-piperazinyl)carbonyl, piperidinocarbonyl or morpholinocarbonyl radical, on the understanding that the alkyl radicals are straight- or branched-chain radicals and contain, except where specifically stated, 1 to 10 carbon atoms, and that the piperazinyl, piperidino, piperidyl and pyrrolidinyl radicals can be unsubstituted or substituted at any position with an alkyl or alkylcarbonyl radical, or can alternatively form a lactam group with the nitrogen atom of the ring.

The following products are of very special value:
[2-(7-chloro-1,8-naphthyridin-2-yl)-3-oxo-1-isoindolinyloxy]-N-(2-methylpropyl)acetamide
[2-(7-chloro-1,8-naphthyridin-2-yl)-3-oxo-1-isoindolinyloxy]-N-propylacetamide
2-(7-chloro-1,8-naphthyridin-2-yl)-3-[2-(4-methyl-1-piperazinyl)- 2-oxoethoxy]-1-isoindolinone
[2-(7-chloro-1,8-naphthyridin-2-yl)-3-oxo-1-isoindolinyloxy]-N,N-pentamethyleneacetamide
2-(7-chloro-1,8-naphthyridin-2-yl)-3-(5-methylhexyloxy)-1-isoindolinone

[2-(7-chloro-1,8-naphthyridin-2-yl)-3-oxo-1-isoin-
dolinyloxy]-N-isopropylacetamide
([2-(7-methoxy-1,8-naphthyridin-2-yl)-3-oxo-1-isoin-
dolinyloxy]-N-butylacetamide.

The examples which follow show how the invention may be put into practice.

EXAMPLE 1

Sodium hydride (0.3 g) is added in small portions at a temperature in the region of 0° C. to a solution, maintained under an argon atmosphere, of 3-hydroxy-2-(7-methoxy-1,8-naphthyridin-2-yl)-1-isoindolinone (3.1 g) in anhydrous dimethylformamide (40 cc). The suspension obtained is stirred for 45 minutes at a temperature in the region of 0° C. and a 1.4M solution (8.5 cc) of N,N-dimethyl-2-chloroethylamine in toluene is then added. The reaction mixture is heated with stirring to a temperature of 65° C. for 4 hours, and is then cooled to a temperature in the region of 10° C., poured into distilled water (350 cc) and extracted with dichloromethane (3×50 cc). The organic phases are combined, washed with distilled water (4×30 cc), dried over magnesium sulphate, filtered and then concentrated to dryness under reduced pressure (2.7 kPa) at 40° C. Ethanol (8 cc) heated to 45° C. is added to the oily residue obtained. After removal of a solid by filtration, fumaric acid (1 g) is added to the filtrate and the mixture is heated until dissolution is complete. The solution obtained is cooled to a temperature in the region of 5° C. for 1 hour. The solid formed is separated by filtration, washed with ethanol (2×5 cc), cooled to a temperature in the region of 0° C., and then with diethyl ether (2×20 cc). Distilled water (200 cc) heated to 40° C. is added to the solid obtained. After removal of a solid by filtration, the filtrate is cooled to a temperature in the region of 10° C., saturated aqueous potassium bicarbonate solution is then added to a pH in the region of 9 and the mixture is extracted with ethyl acetate (3×120 cc). The organic phases are combined, washed with distilled water (3×50 cc), dried over magnesium sulphate, filtered and then concentrated to dryness under reduced pressure (2.7 kPa) at 60° C. The oily residue obtained is dissolved in ethanol (3 cc) heated to 45° C. Fumaric acid (0.4 g) is added to this solution and the mixture is heated until dissolution is complete. The solid obtained is cooled to a temperature in the region of 5° C. for 1 hour. The solid formed is separated by filtration, washed with ethanol (2×1 cc), cooled to a temperature in the region of 0° C., and then with diethyl ether (2×2 cc), and dried in the air. 3-(2-Dimethylaminoethoxy)-2-(7-methoxy-1,8-naphthyridin-2-yl)-1-isoindolinone fumarate (1.4 g), m.p. 205° C., is thereby obtained.

3-Hydroxy-2-(7-methoxy-1,8-naphthyridin-2-yl)1-isoindolinone may be prepared by the method described in Belgian Pat. No. 815,019.

EXAMPLE 2

An oily suspension (50% by weight; 2.1 g) of sodium hydride is added in small portions at a temperature in the region of 0° C. to a solution of 3-hydroxy-2-(7-methoxy-1,8-naphthyridin-2-yl)-1-isoindolinone (12.3 g) in anhydrous dimethylformamide (150 cc). The suspension is stirred for 45 minutes at this temperature. A 1.5N solution (29.4 cc) of 1-chloro-3-dimethylaminopropane in toluene is then added. The mixture is heated to a temperature in the region of 75° C. for 3 hours. The suspension obtained is poured into water (900 cc) and extracted with methylene chloride (3×150 cc). After being washed with water and dried over magnesium sulphate, the organic extracts are concentrated to dryness under reduced pressure (2.7 kPa) at 40° C. The residue obtained is dissolved in methanol (50 cc); the remaining insoluble material is removed by filtration. The filtrate is concentrated to dryness under reduced pressure (2.7 kPa) at 40° C. The residue obtained is dissolved in methanol (50 cc); the remaining insoluble material is removed by filtration. The filtrate is concentrated to dryness under reduced pressure (2.7 kPa) at 70° C. The oily residue obtained is dissolved in ethanol (20 cc). The solution obtained is treated with a solution of fumaric acid (2.8 g) in ethanol (35 cc). After 2 hours at a temperature in the region of 4° C., a crystallized solid (4.7 g) is obtained in 2 crops, and this is purified a first time by recrystallization in ethanol (250 cc). 3.8 g of product are thereby obtained. This product is taken up with water (200 cc) and methylene chloride (100 cc), and the aqueous phase is alkalinized to pH 9 with 4N aqueous sodium hydroxide solution. The product is extracted again with methylene chloride (3×100 cc). After being washed with water and dried over magnesium sulphate, the organic extracts are concentrated to dryness under reduced pressure (2.7 kPa) at 60° C. The oil obtained (2.5 g) is dissolved in ethanol (15 cc). A solution of fumaric acid (0.75 g) in ethanol (10 cc) is added to the solution obtained. The crystallized product which forms is separated by filtration, washed with ethanol (5 cc) and dried under reduced pressure (0.07 kPa) at 45° C. 3-(3-Dimethylaminopropoxy)-2-(7-methoxy-1,8-naphthyridin-2-yl)-1-isoindolinone fumarate (2.5 g), m.p. 215–218° C., is thereby obtained.

EXAMPLE 3

Working in a manner similar to that described in Example 1, but starting with 3-hydroxy-2-(7-methoxy-1,8-naphthyridin-2-yl)-1-isoindolinone (15.4 g), sodium hydride (1.5 g) and a 0.65M solution (32 cc) of 1-(3-chloropropyl)-4-methylpiperazine in toluene, 2-(7-methoxy-1,8-naphthyridin-2-yl)-3-[3-(4-methyl-1-piperazinyl)propoxy]-1-isoindolinone difumarate (5.4 g), m.p. 195° C., is obtained.

1-(3-Chloropropyl)-4-methylpiperazine may be obtained by the method described by HROMATKA O., GRASS I., SAUTER F., Monastsh. Chem., 1956, 87, 701.

EXAMPLE 4

Sodium hydride (0.25 g) is added in small portions at a temperature in the region of 0° C. to a solution, maintained under an argon atmosphere, of 3-hydroxy-2-(7-methoxy-1,8-naphthyridin-2-yl)-1-isoindolinone (3.1 g) in anhydrous dimethylformamide (50 cc). The suspension obtained is stirred for 45 minutes at a temperature in the region of 0° C., and N,N-dimethyl-2chloroacetamide (1.3 g) is then added. The reaction mixture is heated with stirring to a temperature of 70° C. for 3 hours, then cooled to a temperature in the region of 10° C., poured into distilled water (200 cc) and extracted with dichloromethane (3×70 cc). The organic phases are combined, washed with distilled water (2×40 cc), dried over magnesium sulphate, filtered and then concentrated to dryness under reduced pressure (2.7 kPa) at 40° C. After recrystallization in ethyl acetate, N,N-dimethyl-2-[2-(7-methoxy-1,8-naphthyridin-2-yl)-3-oxo-1-isoindolinyloxy]acetamide (2 g), m.p. 166° C., is obtained.

2-Chloro-N,N-dimethylacetamide may be prepared by the method described by JACOBS W. A., HEIDELBERGER M., J. Biol. Chem. 1915, 21, 145.

EXAMPLE 5

An oily suspension (50% by weight; 1.2 g) of sodium hydride is added in small portions at a temperature in the region of 0° C. to a solution, maintained under an argon atmosphere, of 3-hydroxy-2-(7-methoxy-1,8-naphthyridin-2-yl)-1-isoindolinone (6.2 g) in anhydrous dimethylformamide (100 cc). The suspension obtained is stirred for 30 minutes at a temperature in the region of 0° C. and a 1.4M solution (16 cc) of 3-chloromethylpyridine in toluene is then added. The reaction mixture is heated with stirring to a temperature of 70° C. for 1 hour, then cooled to a temperature in the region of 10° C., poured into distilled water (600 cc) and extracted with dichloromethane (3×200 cc). The organic phases are combined, washed with distilled water (4×50 cc), dried over magnesium sulphate, filtered and then concentrated to dryness under reduced pressure (2.7 kPa) at 40° C. 1N aqueous hydrochloric acid solution (30 cc) is added to the residue obtained. After removal of a solid by filtration, the filtrate is alkalinized with 10N aqueous sodium hydroxide solution to a pH in the region of 11, and extracted with dichloromethane (3×150 cc). The organic phases are combined, washed with distilled water (3×25 cc), dried over magnesium sulphate, filtered and then concentrated to dryness under reduced pressure (2.7 kPa) at 40° C. After recrystallization in acetonitrile, 2-(7-methoxy-1,8-naphthyridin-2-yl)-3-[(3-pyridyl)methoxy]-1-isoindolinone (3.7 g), m.p. 175° C., is obtained.

3-Chloromethylpyridine may be prepared by the method described by MOSHER H. S., TESSIERI J. E., J. Am. Chem. Soc., 1951, 73, 4925.

EXAMPLE 6

An oily suspension (50% by weight; 1.5 g) of sodium hydride is added in small portions at a temperature in the region of 0° C. to a solution, maintained under an argon atmosphere, of 4-dimethylaminobutanol (3.6 g) n anhydrous tetrahydrofuran (150 cc). The suspension obtained is stirred for 20 minutes at a temperature in the region of 0° C., and then cooled to a temperature of −10° C. 3-Chloro-2-(7-chloro-1,8-naphthyridin-2-yl)-1-isoindolinone (9.9 g) is then added and stirring is continued for 6 hours at a temperature in the region of 0° C. The reaction mixture is then poured into distilled water (600 cc) and extracted with dichloromethane (3×150 cc). The organic phases are combined, washed with distilled water (3×40 cc) and extracted with 1N aqueous hydrochloric acid solution (3×100 cc). The aqueous phases are combined, alkalinized with 10N aqueous sodium hydroxide solution to a pH in the region of 11 and then extracted with ethyl acetate (3×200 cc). The organic phases are combined, washed with distilled water (4×25 cc), dried over magnesium sulphate, filtered and then concentrated to dryness under reduced pressure (2.7 kPa) at 60° C. The oily residue is dissolved in ethanol (25 cc). Fumaric acid (1.25 g) is added to this solution and the mixture is then heated until dissolution is complete. The solution obtained is cooled to a temperature in the region of 5° C. for 1 hour. The solid formed is separated by filtration, washed with ethanol (2×5 cc), cooled to a temperature in the region of 0° C., and then with diethyl ether (2×20 cc) and dried in the air. 2-(7-Chloro-1,8-naphthyridin-2-yl)-3-(4-dimethylaminobutoxy)1-isoindolinone fumarate (4 g), m.p. 190° C., is thereby obtained.

3-Chloro-2-(7-chloro-1,8-naphthyridin-2-yl)-1-isoindolinone may be prepared in the following manner: sulphinyl chloride (200 cc) is added dropwise with stirring to 3-hydroxy-2-(7-methoxy-1,8-naphthyridin-2-yl)-1-isoindolinone (15.5 g). The reaction mixture is heated to reflux with stirring for 1 hour, then treated with dimethylformamide (0.5 cc) and heated again to reflux for 3 hours, then cooled to a temperature in the region of 60° C. and concentrated to dryness under reduced pressure (2.7 kPa) at 60° C. Dichloromethane (100 cc) is added to the residue obtained and the mixture concentrated to dryness under reduced pressure (2.7 kPa) at 60° C. Dichloromethane (100 cc) is added to the residual solid obtained and the mixture is stirred for 10 minutes. The product is separated by filtration and washed with dichloromethane (15 cc) and then with diisopropyl ether (2×25 cc), and dried in the air. 3-Chloro-2-(7-chloro-1,8-naphthyridin-2-yl)-1-isoindolinone (12.4 g), which has not melted at 300° C., is thereby obtained.

4-Dimethylaminobutanol may be prepared by the method described by SZARVASI E., Bull. Soc. Chim. France, (1949), 647.

EXAMPLE 7

An oily suspension (50% by weight; 1.5 g) of sodium hydride is added in small portions at a temperature in the region of 0° C. to a solution, maintained under an argon atomosphere, of 3-dimethylamino-1-propanol (3.1 g) in anhydrous tetrahydrofuran (75 cc), and the suspension obtained is stirred for 30 minutes at a temperature in the region of 0° C. 3-Chloro-2-(7-chloro-1,8-naphthyridin-2-yl)-1-isoindolinone (10.1 g) is then added and stirring is continued for 16 hours at a temperature in the region of 20° C. The reaction mixture is then concentrated to dryness under reduced pressure (2.7 kPa) at 40° C. The residue obtained is poured into distilled water (200 cc) and extracted with dichloromethane (3×150 cc). The organic phases are combined, washed with distilled water (2×25 cc), dried over magnesium sulphate, filtered and then concentrated to dryness under reduced pressure (2.7 kPa) at 40° C. The oily residue obtained is dissolved in 2-propanol (100 cc) and the solution obtained is treated with a 4N solution (7.65 cc) of hydrochloric acid in diethyl ether. The solid formed is separated by filtration, washed with 2-propanol (3×15 cc) and then with diisopropyl ether (3×25 cc), and dried under reduced pressure (0.07 kPa) at 40° C. The product thereby obtained is recrystallized twice, first in 2-propanol and then in a mixture of acetonitrile and diisopropyl ether (60:40 by volume). 2-(7-Chloro-1,8-naphthyridin-2-yl)-3-(3-dimethylaminopropoxy)-1-isoindolinone hydrochloride (6.3 g), m.p. 204° C., is thereby obtained.

EXAMPLE 8

Sodium hydride (0.9 g) is added in small portions at a temperature in the region of −10° C. to a solution, maintained under an argon atmosphere, of 2-(2-pyridyl)ethanol (4.4 g) in anhydrous tetrahydrofuran (100 cc), and the suspension obtained is stirred for 30 minutes at a temperature in the region of −5° C. 3-Chloro-2-(7-chloro-1,8-naphthyridin-2-yl)-1-isoindoline (9.9 g) is then added and stirring is continued for 2 hours at a temperature in the region of 0° C. The reaction mixture is then poured into distilled water (400 cc) and extracted with dichloromethane (4×150 cc). The organic phases are combined, washed with distilled water (2×25 cc), dried over magnesium sulphate, filtered and then concentrated to dryness under reduced pressure (2.7 kPa) at 40° C. After recrystallization in ethanol, 2-(7-chloro-1,8-naphthyridin-2-yl)-3-[2-(2-pyridyl)ethoxy]-1-isoindolinone (5 g), m.p. 142° C., is obtained.

EXAMPLE 9

Sodium hydride (1.1 g) is added in small portions at a temperature in the region of −5° C. to a solution, maintained under an argon atmosphere, of 3-hydroxy-N,N-dimethylpropanamide (5.4 g) in anhydrous tetrahydrofuran (175 cc), and the suspension obtained is stirred for 30 minutes at a temperature in the region of 0° C. 3-Chloro-2-(7-chloro-1,8-naphthyridin-2-yl)-1-isoindolinone (11.5 g) is then added and stirring is continued for 3 hours at a temperature in the region of 20° C. The reaction mixture is then poured into distilled water (600 cc) and extracted with dichloromethane (3×200 cc). The organic phases are combined, washed with distilled water (3×75 cc), dried over magnesium sulphate, filtered and concentrated to dryness under reduced pressure (2.7 kPa) at 60° C. The oily residue obtained is purified by chromatography on silica gel (100 g) contained in a column 3 cm in diameter [eluant: dichloromethane/methanol (97:3 by volume)]. Elution is first performed with 100 cc of solvent: the corresponding eluate is dicarded; elution is then performed with 600 cc of solvent: the corresponding eluate is concentrated to dryness under reduced pressure (2.7 kPa) at 40° C. After recrystallization in acetonitrile 3-[2-(7-chloro-1,8-naphthyridin-2-yl)-3-oxo-1-isoindolinyloxy]-N,N-dimethylpropanamide (4.7 g), m.p. 168° C., is obtained.

3-Hydroxy-N,N-dimethylpropanamide may be prepared by the method described in U.S. Pat. No. 2,548,156.

EXAMPLE 10

Working in a manner similar to that described in Example 9, but starting with 4-methyl-1-pentanol (2.1 g), sodium hydride (0.5 g) and 3-chloro-2-(7-chloro-1,8-naphthyridin-2-yl)-1-isoindolinone (5.3 g), 2-(7-chloro-1,8-naphthyridin-2-yl)-3-(4-methylpentyloxy)-1-isoindolinone (3.3 g), m.p. 104° C., is obtained.

EXAMPLE 11

Working in a manner similar to that described in Example 6, but starting with 1-(3-hydroxypropionyl)-4-methylpiperazine (7.35 g), an oily suspension (50% by weight; 2.1 g) of sodium hydride, 3-chloro-2-(7-chloro-1,8-naphthyridin-2-yl)-1-isoindolinone (11.5 g) and fumaric acid (1.75 g), 2-(7-chloro-1,8-naphthyridin-2-yl)-3-[2-(4-methyl-1-piperazinylcarbonyl)ethoxy]-1-isoindolinone fumarate (7.4 g) is obtained, which is dissolved in distilled water (350 cc). The aqueous solution thereby obtained is alkalinized with 10N aqueous sodium hydroxide solution to a pH in the region of 11, and then extracted with ethyl acetate (3×200 cc). The organic phases are combined, washed with distilled water (3×300 cc), dried over magnesium sulphate, filtered and concentrated to dryness under reduced pressure (2.7 kPa) at 60° C. After recrystallization in ethyl acetate, 2-(7-chloro-1,8-naphthyridin-2-yl)-3-[2-(4-methyl-1-piperazinylcarbonyl)ethoxy]-1-isoindolinone (2.8 g), m.p. 150° C., is obtained.

1-(3-Hydroxypropionyl)-4-methylpiperazine may be prepared in the following manner: β-propionlactone (3.15 g) is added dropwise at a temperature in the region of −5° C. to a solution, maintained under an argon atmosphere, of N-methylpiperazine (7 cc) in anhydrous diethyl ether (130 cc), and the mixture is stirred for one hour at a temperature in the region of 20° C. The reaction mixture is then filtered and the filtrate is concentrated to dryness under reduced pressure (2.7 kPa) at 40° C. 1-(3-Hydroxypropionyl)-4-methylpiperazine (8.6 g) is thereby obtained in the form of an oil, which is used in the crude state in the subsequent syntheses.

EXAMPLE 12

Working in a manner similar to that described in Example 6, but starting with 1-methyl-4-piperidinol (4.3 g), sodium hydride (0.9 g) and 3-chloro-2-(7-chloro-1,8-naphthyridin-2-yl)-1-isoindolinone (12.4 g), and heating the reaction mixture for 90 minutes under reflux, 2-(7-chloro-1,8-naphthyridin-2-yl)-3-(1-methyl-4-piperidyloxy)-1-isoindolinone (3 g), m.p. 204° C., is obtained after recrystallization in ethanol.

EXAMPLE 13

Working in a manner similar to that described in Example 6, but starting with 2-(1-imidazolyl)ethanol (3.5 g), an oily suspension (50% by weight; 1.8 g) of sodium hydride and 3-chloro-2-(7-chloro-1,8-naphthyridin-2-yl)-1-isoindolinone (8.25 g), and stirring the reaction mixture for 3 hours at a temperature in the region of 20° C., 2-(7-chloro-1,8-naphthyridin-2-yl)-3-[2-(1-imidazolyl)-ethoxy]-1-isoindolinone (4.9 g), m.p. 198° C., is obtained after recrystallization in ethanol.

2-(1-Imidazolyl)ethanol may be prepared by the method described by GIESEMANN H., J. Prakt. Chem., 1957, 4 (4), 169.

EXAMPLE 14

Working in a manner similar to that described in Example 9, but starting with 1-acetyl-4-(2-hydroxyethyl)piperidine (20 g), sodium hydride (2.1 g) and 3-chloro-2-(7-chloro-1,8-naphthyridin-2-yl)-1-isoindolinone (11.6 g), 3-[2-(1-acetyl-4-piperidyl)ethoxy]-2-(7-chloro-1,8-naphthyridin-2-yl)-1-isoindolinone (3.9 g), m.p. 155° C., is obtained after recrystallization in ethyl acetate.

1-Acetyl-4-(2-hydroxyethyl)piperidine may be prepared by the method described by MEYER W. L., and OLSEN R. G., Can. J. Chem., 1967, 45 (13), 1459.

EXAMPLE 15

Working in a manner similar to that described in Example 6, but starting with 2-(1-methyl-4-piperidyl)ethanol (5.4 g), an oily suspension (50% by weight; 1.8 g) of sodium hydride and 3-chloro-2-(7-chloro-1,8-naphthyridin-2-yl)-1-isoindolinone (9.9 g), and stirring the reaction mixture for 2 hours at a temperature in the region of 20° C., 2-(7-chloro-1,8-naphthyridin-2-yl)-3-[2-(1-methyl-4-piperidyl)ethoxy]-1-isoindolinone (3.65 g), m.p. 185° C., is obtained after recrystallization in acetonitrile.

2-(1-Methyl-4-piperidyl)ethanol may be prepared by the method described by KATMETANI T. et al., 1968, 88 (5), 573. Chem. Abstr., 1969, 70, 3790p.

EXAMPLE 16

Working in a manner similar to that described in Example 9, but starting with 3-methyl-1-butanol (2.7 g), sodium hydride (0.75 g) and 3-chloro-2-(7-chloro-1,8-naphthyridin-2-yl)-1-isoindolinone (6.6 g), 2-(7-chloro- 1,8naphthyridin-2-yl)-3-(3-methylbutoxy)-1-isoindolinone (4.7 g), m.p. 95° C., is obtained after recrystallization in diisopropyl ether.

EXAMPLE 17

Working in a manner similar to that described in Example 9, but starting with 1-pentanol (3.32 g), sodium hydride (0.9 g) and 3-chloro-2-(7-chloro-1,8-naphthyridin-2-yl)-1-isoindolinone (8.25 g), 2-(7-chloro-1,8-naphthyridin-2-yl)-3-pentyloxy-1-isoindolinone (5 g), m.p. 98° C., is obtained after recrystallization in a mixture of ethyl acetate and diisopropyl ether (2:1 by volume).

EXAMPLE 18

Working in a manner similar to that described in Example 9, but starting with 5-methyl-1-hexanol (3.6 g), sodium hydride (0.72 g) and 3-chloro-2-(7-chloro-1,8-naphthyridin-2-yl)-1-isoindolinone (6.6 g), 2-(7-chloro-1,8-naphthyridin-2-yl)-3-(5-methylhexyloxy)-1-isindolinone (5.7 g), m.p. 96° C., is obtained after recrystallization in diisopropyl ether.

5-Methyl-1-hexanol may be prepared by the method described by GRIGNARD V., C.R. Acad. Sc. Paris, 1903, 136, 1260.

EXAMPLE 19

Working in a manner similar to that described in Example 9, but starting with 3-cyclohexylpropanol (11.4 g), sodium hydride (1.44 g) and 3-chloro-2-(7-chloro-1,8-naphthyridin-2-yl)-1-isoindolinone (13.2 g), 2-(7-chloro-1,8--naphthyridin-2-yl)-3-(3-cyclohexylpropoxy)-1-isoindolinone (9.8 g), m.p. 123° C., is obtained after recrystallization in ethanol.

3-Cyclohexylpropanol may be prepared by the method described by HIERS G. S. and ADAMS R., J. Am. Chem. Soc., 1926, 48, 2385.

EXAMPLE 20

Working in a manner similar to that described in Example 9, but starting with 3-methoxypropanol (3.6 g), sodium hydride (1.2 g) and 3-chloro-2-(7-chloro-1,8-naphthyridin-2-yl)-1-isoindolinone (13.2 g), and stirring the reaction mixture for 4 hours under reflux of tetrahydrofuran, 2-(7-chloro-1,8-naphthyridin-2-yl)-3-(3-methoxypropoxy)-1-isoindolinone (5.8 g), m.p. 117° C., is obtained after two successive recrystallizations in ethanol.

3-Methoxypropanol may be prepared by the method described by PUMMERER R., SCHONAMSGRUBER M., Chem. Ber., 1939, 72, 1838.

EXAMPLE 21

Working in a manner similar to that described in Example 9, but starting with 4-methyl-3-pentenol (6 g), sodium hydride (1.1 g) and 3-chloro-2-(7-chloro-1,8-naphthyridin-2-yl)-1-isoindolinone (9.9 g), 2-(7-chloro-1,8-naphthyridin-2-yl)-3-(4-methyl-3pentenyloxy)-1-isoindolinone (6.6 g), m.p. 138° C., is obtained after recrystallization in ethanol.

4-Methyl-3-pentenol may be prepared by the method described by ROGAN J. B., J. Org. Chem., 1962, 27, 3910.

EXAMPLE 22

An oily suspension (50% by weight; 2.2 g) of sodium hydride is added in small portions at a temperature in the region of 0° C. to a solution, maintained under a nitrogen atmosphere, of N,N-pentamethyleneglycolamide (6.5 g) in anhydrous tetrahydrofuran (300 cc), and 3-chloro-2-(7-chloro-1,8-naphthyridin-2-yl)-1-isoindolinone (15 g) is then added. The reaction mixture is then stirred for 18 hours at a temperature in the region of 20° C. and poured into water (1500 cc). The precipitate obtained is separated by filtration and purified by chromatography on silica (0.063–0.2 mm; 400 g) contained in a column 5 cm in diameter [eluant: methylene chloride/methanol (95:5 by volume)], collecting 100-cc fractions. Fractions 21 to 61 are combined and concentrated to dryness under reduced pressure (2.7 kPa). After recrystallization in 2-propanol and then acetonitrile, [2-(7-chloro-1,8-naphthyridin-2-yl)-3-oxo-1-isoindolinyloxy]-N,N-pentamethyleneacetamide (7.3 g), m.p. 185° C., is obtained.

N,N-Pentamethyleneglycolamide may be obtained in the following manner: a solution of methyl glycolate (15 g) and piperidine (15.8 g) is stirred for 48 hours at a temperature in the region of 20° C. The reaction mixture is then concentrated to dryness under reduced pressure (2.7 kPa). N,N-Pentamethyleneglycolamide (22.8 g) is thereby obtained in the form of an oil, which is employed in the crude form in the subsequent syntheses.

EXAMPLE 23

The procedure is as in Example 7, but starting with 1-hydroxyacetyl-4-methylpiperazine (5.3 g) in tetrahydrofuran (200 cc), an oily suspension (50% by weight; 1.5 g) of sodium hydride and 3-chloro-2-(7-chloro-1,8-naphthyridin-2-yl)-1-isindolinone (10 g). The residue obtained is purified by crystallization in acetonitrile and then by recrystallization in 2-propanol. 2-(7-chloro-1,8-naphthyridin-2-yl)-3-[2-(4-methyl-1-piperazinyl)-2-oxoethoxy]-1-isoindolinone (3.8 g), m.p. 175° C., is thereby obtained.

1-Hydroxyacetyl-4-methylpiperazine may be prepared according to the method described in Example 22 for the preparation of N,N-pentamethyleneglycolamide, but starting with methylglycolate (14 g) and N-methylpiperazine (16 g). 1-Hydroxyacetyl-4-methylpiperazine (20.2 g) is thereby obtained in the form of an oil, which is employed in the crude state in the subsequent syntheses.

EXAMPLE 24

The procedure is as in Example 22, but starting with 1-acetyl-4-hydroxymethylpiperidine (4.7 g) in anhydrous tetrahydrofuran (200 cc), an oily suspension (50% by weight; 1.45 g) of sodium hydride and 3-chloro-2-(7-chloro-1,8-naphthyridin-2-yl)-1-isoindolinone (9.9 g). The product obtained is purified by flash chromatography on silica (0.040–0.063 mm; 100 g) contained in a column 3 cm in diameter [eluant: ethyl acetate/methanol (98:2 by volume)], collecting 50-cc fractions under a pressure of 0.3 bar. Fractions 75 to 140 are concentrated to dryness under reduced pressure (2.7 kPa). The product obtained is purified again by flash chromatography on silica (0.040–0.063 mm; 110 g) containing in a column 3 cm in diameter (eluant: ethyl acetate), collecting 50-cc fractions under a pressure of 0.3 bar. Fractions 51 to 150 are concentrated to dryness under reduced pressure (2.7 kPa).

The solid obtained is crystallized by stirring in water and then in ethyl acetate, and 3-[(1-acetyl-4-piperidyl)-methoxy]-2-(7-chloro-1,8-naphthyridin-2-yl)- 1-isoindolinone (3.3 g), m.p. 160° C., is thereby obtained.

1-Acetyl-4-hydroxymethylpiperidine may be obtained in the following manner: acetic anhydride (20.5 cc) is added in the course of 15 minutes to a solution of hydroxymethylpiperidine (23.8 g) in ethanol (100 cc) at a temperature in the region of 10° C., and the mixture is stirred for 18 hours at a temperature in the region of 20° C. The reaction mixture is concentrated to dryness under reduced pressure (2.7 kPa); the residue obtained is taken up with water (50 cc) and potassium carbonate (50 g), and the solution is extracted with methylene chloride (3×150 cc); the organic extracts are combined, dried and concentrated to dryness under reduced pressure (2.7 kPa). 1-Acetyl-4-hydroxymethylpiperidine (33.6 g) is thereby obtained in the form of an oil, which is employed in the crude state in the subsequent syntheses.

EXAMPLE 25

Working as in Example 22 but starting with 1-hydroxyacetyl-4-methylpiperidine (7 g) in tetrahydrofuran (250 cc), an oily suspension (50% by weight; 2.3 g) of sodium hydride and 3-chloro-2-(7-chloro-1,8-naphthyridin-2-yl)-3[2-(4-methylpiperidino)-2-oxoethoxy]-1-isoindolinone (2.3 g), m.p. 170° C., is obtained after recrystallization in 2-propanol.

1-Hydroxyacetyl-4-methylpiperidine may be prepared as in Example 22 for N,N-pentamethyleneglycolamide, but starting with methylglycolate (14 g) and 4-methylpiperidine (15.9 g). 1-Hydroxyacetyl-4-methylpiperidine (21.8 g) is thereby obtained in the form of an oil, which is employed in the crude state in the subsequent syntheses.

EXAMPLE 26

An oily suspension (50% by weight; 2.1 g) of sodium hydride is added at a temperature in the region of 0° C. to a solution, maintained under a nitrogen atmosphere, of 3-hydroxy-2-(7-methoxy-1,8-naphthyridin-2-yl)-1-isoindolinone (12.3 g) in anhydrous dimethylformamide (150 cc). The suspension obtained is stirred for 45 minutes at a temperature in the region of 0° C., N-(cyclohexyl)chloroacetamide (7.7 g) is then added and the mixture is heated to 80° C. for 18 hours. After being cooled, the reaction mixture is poured into water (700 cc) and the precipitate obtained is separated by filtration, washed with water and dried in the air. The solid obtained is purified by chromatography on silica (0.063–0.2 mm; 220 g) contained in a column 4 cm in diameter (eluant: methylene chloride), collecting 50-cc fractions. Fractions 41 to 60 are combined and concentrated to dryness under reduced pressure (2.7 kPa). By recrystallization of the residue obtained in acetonitrile, [2-(7-methoxy-1,8-naphthyridin-2-yl)-3-oxo-1-isoindolinyloxy]-N-cyclohexylacetamide (1.8 g), m.p. 175° C., is obtained.

N-(Cyclohexyl)chloroacetamide may be prepared in the following manner: chloroacetyl chloride (11.3 g) is introduced in the course of 20 minutes into a solution of cyclohexylamine (9.9 g) and triethylamine (15.2 g) in methylene chloride (50 cc), the temperature being maintained in the region of 10° C. The mixture is then stirred for 2 hours at a temperature in the region of 20° C. and then poured into water (100 cc). The organic phase is separated, washed with water and concentrated to dryness under reduced pressure (2.7 kPa). N-(Cyclohexyl)chloroacetamide (14.7 g) is thereby obtained in the form of an oil, which is employed in the crude state in the subsequent syntheses.

EXAMPLE 27

An oily suspension (50% by weight; 1.6 g) of sodium hydride is added at a temperature in the region of 0° C. to a solution, maintained under a nitrogen atmosphere, of 3-hydroxy-2-(7-methoxy-1,8-naphthyridin-2-yl)-1-isoindolinone (9.2 g) in anhydrous dimethylformamide (120 cc). The suspension obtained is stirred for 45 minutes at a temperature in the region of 0° C., and 1-chloroacetyl-4-propionylpiperazine (7.2 g) is then added. The reaction mixture is heated to 80° C. for 20 hours and then cooled and poured into water (700 cc). The product is then extracted with methylene chloride (3×200 cc). The organic extracts are combined, washed with water, dried and concentrated to dryness under reduced pressure (2.7 kPa).

The residue obtained is crystallized by stirring in 2-propanol, and then purified by recrystallization first in carbon tetrachloride and then in ethanol. 2-(7-Methoxy-1,8-naphthyridin-2-yl)-3-[2-(4-propionyl-1-piperazinyl)-2-oxoethoxy]-1-isoindolinone (2.3 g), m.p. 160° C., is thereby obtained.

1-Chloroacetyl-4-propionylpiperazine may be prepared according to the method described in Example 26 for the preparation of N-(cyclohexyl)chloroacetamide, but starting with chloroacetyl chloride (4.5 g), 1-propionylpiperazine (7.1 g), triethylamine (9.1 g) and methylene chloride (20 cc). 1-Chloroacetyl-4-propionylpiperazine (7.2 g), m.p. 80° C., is thereby obtained.

EXAMPLE 28

The procedure is as in Example 22, but starting with 1-hydroxyacetyl-4-isopropylpiperazine (9.4 g) in tetrahydrofuran (250 cc), an oily suspension (50% by weight; 2.3 g) of sodium hydride and 3-chloro-2-(7-chloro-1,8-naphthyridin-2-yl)-1-isoindolinone (10 g). After two successive recrystallizations in ethanol, 2-(7-chloro-1,8-naphthyridin-2-yl)-3-[2-(4-isopropyl-piperazino)-2oxoethoxy]-1-isoindolinone (2 g), m.p. 186° C., is obtained.

1-Hydroxyacetyl-4-isopropylpiperazine may be prepared according to the method described in Example 22 for the preparation of N,N-pentamethyleneglycolamide, but starting with methyl glycolate (7 g) and 1-isopropylpiperazine (11.1 g). 1-Hydroxyacetyl-4-isopropylpiperazine (15.7 g) is thereby obtained in the form of an oil, which is employed in the crude state in the subsequent syntheses.

EXAMPLE 29

An oily suspension (50% by weight; 1.8 g) of sodium hydride is added in small portions at a temperature in the region of -5° C. to a solution, maintained under an argon atmosphere, of 3-hydroxy-2-(7-methoxy-1,8-naphthyridin-2-yl)-1-isoindolinone (9.3 g) in anhydrous dimethylformamide (120 cc), and the suspension obtained is stirred for 30 minutes at a temperature in the region of 0° C. 1-Chloro-4-methyl-2-pentanone (8.1 g) is then added dropwise while the temperature is maintained at 0° C., and stirring is continued for a further 1 hour at 0° C. and then for 4 hours at a temperature in the region of 20° C. The reaction mixture is then poured into a mixture of ice (150 g) and water (350 cc), neutralized with 1N hydrochloric acid solution and extracted with dichloromethane (3×250 cc). The organic phases are combined, washed with water (4×75 cc), dried over magnesium sulphate, filtered and then concentrated to dryness under reduced pressure (2.7 kPa) at 40° C. The residue obtained is taken up with ethyl acetate (25 cc) and the insoluble product is separated by filtration, washed successively with ethyl acetate (10 cc) and diisopropyl ether (10 cc) and then discarded. The filtrate is concentrated to dryness under reduced pressure (2.7 kPa) at 40° C. The residue obtained is purified by chromatography on silica (120 g) contained in a column 3 cm in diameter [eluant: dichloromethane/methanol (98.5:1.5 by volume)]. Elution is first performed with 170 cc of solvent: the corresponding eluate is discarded; elution is then performed with 800 cc of solvent and the corresponding eluate concentrated to dryness under reduced pressure (2.7 kPa). After recrystallization of the residue in ethyl acetate, 2-(7-methoxy-1,8-naphthyridin-2-yl)-3-(4-methyl-2-oxopentyloxy)-1isoindolinone (3 g), m.p. 120° C., is obtained. 1-Chloro-4-methyl-2-pentanone may be prepared by the method described by ASINGER F., et al., Ann. Chem., 1964, 672, 156.

EXAMPLE 30

The procedure is as in Example 22, but starting with N-isopropylglycolamide (5.3 g) in tetrahydrofuran (250 cc), an oily suspension (50% by weight; 2.2 g) of sodium hydride and 3-chloro-2-(7-chloro-1,8-naphthyridin-2-yl)-1-isoindolinone (10 g). After purification by recrystallization in acetonitrile, [2-(7-chloro-1,8-naphthyridin-2-yl)-3-oxo-1-isoindolinyloxy]-N-isopropylacetamide (4 g), m.p. 188° C., is obtained.

N-Isopropylglycolamide may be prepared according to the method described in Example 22 for the preparation of N,N-pentamethyleneglycolamide, but starting with methylglycolate (14 g) and isopropylamine (9.5 g). N-Isopropylglycolamide (17.5 g) is thereby obtained in the form of an oil, which is employed in the crude state in the subsequent syntheses.

EXAMPLE 31

The procedure is as in Example 22, but starting with N-(3-hydroxypropyl)-2-piperidone (7 g) in anhydrous tetrahydrofuran (150 cc), an oily suspension (50% by weight; 2.15 g) of sodium hydride and 3-chloro-2-(7-chloro-1,8-naphthyridin-2-yl)-1-isoindolinone (10 g). The product obtained is purified by chromatography on silica (0.063–0.2 mm; 240 g) contained in a column 5 cm in diameter, collecting 50-cc fractions. Fractions 23 to 27, eluted with a mixture of methylene chloride and methanol (95:5 by volume), are concentrated to dryness under reduced pressure (2.7 kPa) at 40° C. The residue obtained is crystallized by stirring in acetonitrile and then recrystallized in carbon tetrachloride. 2-(7-Chloro-1,8-naphthyridin-2-yl)-3-[3-(2-oxopiperidino)propoxy]-1-isoindolinone (2 g), m.p. 140° C., is thereby obtained.

N-(3-Hydroxypropyl)piperidone may be prepared according to the method described by PARHAM W. E. and ANDERSON E. L., J. Am. Chem. Soc. 70, 4187 (1948).

EXAMPLE 32

The procedure is as in Example 26, but starting with 3-hydroxy-2-(7-methoxy-1,8-naphthyridin-2-yl)-1-isoindolinone (12.3 g) in dimethylformamide (150 cc), an oily suspension (50% by weight; 2.4 g) of sodium hydride and N-chloroacetylmorpholine (8.2 g). The residue obtained is purified initially by chromatography on silica (0.063–0.2 mm; 180 g) contained in a column 4 cm in diameter [eluant: methylene chloride/methanol mixture (95:5 by volume)], collecting 100-cc fractions. Fractions 190 to 210 are combined and concentrated to dryness under reduced pressure (2.7 kPa). The residue obtained is purified again by flash chromatography on silica (0.040–0.063 mm; 82 g) contained in a column 3 cm in diameter (eluant: methylene chloride/methanol [98:2 by volume)], collecting 10-cc fractions. Fractions 220 to 235 are combined and concentrated to dryness under reduced pressure (2.7 kPa) at 40° C. The solid obtained is recrystallized successively in acetonitrile and in ethanol. 2-(7-Methoxy-1,8-naphthyridin-2-yl)-3-(2-morpholino-2-oxoethoxy)-1-isoindolinone (2 g), m.p. 192° C., is thereby obtained.

N-Chloroacetylmorpholine may be prepared according to the method described in Example 26 for the preparation of N-(cyclohexyl)chloroacetamide, but starting with chloroacetyl chloride (11.3 g), morpholine (8.7 g), triethylamine (15.2 g) and methylene chloride (50 cc). N-Chloroacetylmorpholine (13.7 g) is thereby obtained in the form of an oil, which is employed in the crude state in the subsequent syntheses.

EXAMPLE 33

The procedure is as in Example 22, but starting with N-propylglycolamide (9.4 g) in tetrahydrofuran (375 cc), an oily suspension (50% by weight; 3.3 g) of sodium hydride and 3-chloro-2-(7-chloro-1,8-naphthyridin-2-yl)-1-isoindolinone (15 g). After recrystallization in acetonitrile, [2-(7-chloro-1,8-naphthyridin-2-yl)-3-oxo-1isoindolinyloxy]-N-propylacetamide (10.5 g), m.p. 167° C., is obtained.

N-Propylglycolamide may be prepared according to the method described in Example 22 for the preparation of N,N-pentamethyleneglycolamide, but starting with methylglycolate (18 g) and propylamine (18 cc). N-Propylglycolamide (22.2 g) is thereby obtained in the form of an oil, which is employed in the crude state in the subsequent syntheses.

EXAMPLE 34

The procedure is as in Example 22, but starting with N-(2-methylpropyl)glycolamide (8.9 g) in tetrahydrofuran (357 cc), an oily suspension (50% by weight; 3.3 g) of sodium hydride and 3-chloro-2-(7-chloro-1,8-naphthyridin-2-yl)-1-isoindolinone (15 g). After recrystallization in ethanol, [2-(7-chloro-1,8-naphthyridin-2-yl)-3-oxo-1isoindolinyloxy]-N-(2-methylpropyl)acetamide (10.1 g), m.p. 146° C., is obtained.

N-(2-Methylpropyl)glycolamide may be prepared according to the method described in Example 22 for the preparation of N,N-pentamethyleneglycolamide, but starting with methylglycolate (15 g) and isobutylamine (13.5 g). N-(2-Methylpropyl)glycolamide (21.9 g) is thereby obtained in the form of an oil, which is employed in the crude state in the subsequent syntheses.

EXAMPLE 35

The procedure is as in Example 7, but starting with 4-(2,6-dimethyl-1-piperidyl)butanol (8 g) in anhydrous tetrahydrofuran (220 cc), an oily suspension (50% by weight; 1.9 g) of sodium hydride and 3-chloro-2-(7-chloro-1,8-naphthyridin-2-yl)-1-isoindolinone (8.6 g). The residue obtained is taken up with ethyl acetate (20 cc); the insoluble product is removed by filtration and the filtrate is concentrated to dryness under reduced pressure (2.7 kPa) at 40° C. The residue obtained is taken up with water (50 cc) and 4N aqueous hydrochloric acid solution (20 cc); the remaining insoluble product is removed by filtration. The filtrate is neutralized with 4 N aqueous sodium hydroxide solution and then extracted with methylene chloride (3×100 cc); the organic extracts are combined and washed with water, dried and concentrated to dryness under reduced pressure (3 kPa) at 40° C. The residue obtained is recrystallized successively in ethyl acetate and 2-propanol, and 2-(7-chloro-1,8-naphthyridin-2-yl)-3-[4-(2,6-dimethyl-piperidino)butoxy]-1isoindolinone hydrochloride (1.6 g) is thereby obtained.

4-(2,6-Dimethyl-1-piperidyl)butanol may be prepared in the following manner: a solution of ethyl 4-(2,6-dimethyl-1-piperidyl)butyrate (15 g) in ethyl ether (50 cc) is added in the course of 45 minutes to a suspension of lithium aluminium hydride (5 g) in ethyl ether (250 cc) under reflux of the ether, and the mixture is stirred for 2 hours under reflux. After the mixture is cooled, there is added, in the course of 30 minutes, ethyl acetate (20 cc) followed successively by water (5 cc), 4N aqueous sodium hydroxide solution (5 cc) and water (15 cc). The insoluble product is removed by filtration and washed with ether; the filtrate is dried over sodium sulphate and then concentrated to dryness under reduced pressure (2.7 kPa) at 40° C. 4-(2,6-dimethyl-1-piperidyl)butanol 8 g) is thereby obtained in the form of an oil, which is employed in the crude state in the subsequent syntheses.

Ethyl 4-(2,6-dimethyl-1-piperidyl)butyrate may be prepared in the following manner;

A mixture of ethyl 3-bromo-propionate(25.8g), 2,6-dimethyl-piperidine (30 g) and ethanol (40 cc) is heated for 2 hours under reflux. The reaction mixture is concentrated to dryness under reduced pressure (2.7 kPa) and the residue is taken up in 5N sodium hydroxide solution (30 cc) and then extracted with methylene chloride (3×50 cc). The organic phase is dried over magnesium sulphate, filtered, and concentrated to dryness under reduced pressure (2.7 kPa) at 40° C. Ethyl 4-(2,6-dimethyl-1-piperidyl)butyrate(29 g) is thus obtained as an oil which can be employed in the subsequent synthesis without purification.

EXAMPLE 36

Working as in Example 4, but starting with 3-hydroxy-2-(7-methoxy-1,8-naphthyridin-2-yl)-1-isoindolinone (15.4), an oily suspension (50% by weight; 3 g) of sodium hydride and 2-chloro-1-cyclohexyl-1-ethanone (16), and stirring the reaction mixture for 16 hours at a temperature in the region of 20° C., 3-(2-cyclohexyl-2-oxoethoxy)-2-(7-methoxy-1,8-naphthyridin-2-yl)-1-isoindolinone (8.4 g), m.p. 176° C., is obtained after recrystallization in acetonitrile.

2-Chloro-1-cyclohexyl-1-ethanone may be prepared by the method described by MOUSSERON M. et al., Bull. Soc. Chim. Fr., (1952), 767.

EXAMPLE 37

Working as in Example 4, but starting with 3-hydroxy-2-(7-methoxy-1,8-naphthyridin-2-yl)-1-isoindolinone (9.3 g), an oily suspension (50% by weight; 1.8 g) of sodium hydride and 1-chloro-5-methyl-2-hexanone (9 g), 2-(7-methoxy-1,8-naphthyridin-2-yl)-3-(5-methyl-2-oxo-hexyloxy)-1-isoindolinone (3.6 g), m.p. 120° C., is obtained after recrystallization in ethyl acetate.

1-Chloro-5-methyl-2-hexanone may be prepared by the method described by DETOEUF A., Bull. Soc. Chim. Fr., (1922), 31, 174.

EXAMPLE 38

Sodium hydride (1.1 g) is added in small portions at a temperature in the region of -20° C. to a solution, maintained under an argon atmosphere, of 4-methylpentanethiol (7.1 g) in anhydrous tetrahydrofuran (125 cc), and the suspension obtained is stirred for 1 hour at a temperature in the region of 20° C. 3-chloro-2-(7-chloro-1,8-naphthyridin-2-yl)-1-isoindolinone (9.9 g) is then added and stirring of the reaction mixture is then continued for 2 hours at a temperature in the region of 20° C. The reaction mixture is treated with water (100 cc) and ethyl acetate (100 cc) which have been cooled to a temperature in the region of 0° C. The aqueous phase is separated after settling has occurred and extracted with ethyl acetate (2×100 cc). The organic phases are combined, washed with water (4×50 cc), dried over magnesium sulphate, filtered and concentrated to dryness under reduced pressure (2.7 kPa) at 40° C. The residue obtained is purified by 6 successive recrystallizations in anhydrous ethanol. 2-(7-Chloro-1,8-naphthyridin-2-yl)-3-(4-methyl-pentylthio)-1-isoindolinone (1.1 g), m.p. 141° C., is thereby obtained.

4-Methylpentanethiol may be prepared by the method described by BORDWELL F. G. and HEWETT W. A., J. Org. Chem., (1957), 22, 980.

3-Chloro-2-(7-chloro-1,8-naphthyridin-2-yl)-1-isoindolinone may be prepared as described in Example 6.

EXAMPLE 39

3-Dimethylaminopropylamine (4.1 g) is added at a temperature in the region of 20° C. to a suspension of 3-chloro-2-(7-chloro-1,8-naphthyridin-2-yl)-1-isoindolinone (6.6 g) in anhydrous tetrahydrofuran (100 cc), and the reaction mixture is heated to reflux for 6 hours. After the reaction mixture has been stirred for a further 20 hours at a temperature in the region of 20° C., it is filtered. The isolated solid is washed with ethyl acetate (3×25 cc). The filtrate is washed with distilled water (3×25 cc), dried over magnesium sulphate, filtered and concentrated to dryness under reduced pressure (2.7 kPa) at 60° C. 1N aqueous hydrochloric acid solution (20 cc) is added to the residue obtained. An insoluble product is separated by filtration, washed with 1N aqueous hydrochloric acid solution (2×5 cc) and then discarded. The aqueous filtrates are combined and alkalinized with a saturated aqueous potassium bicarbonate solution to a pH in the region of 8, and then extracted with ethyl acetate (3×40 cc). The organic phases are combined, dried over magnesium sulphate, filtered and then concentrated to dryness under reduced pressure (2.7 kPa) at 60° C. After recrystallization in ethyl acetate, 2-(7-chloro-1,8-naphthyridin-2-yl)-3-(3-dimethylaminopropylamino)-1-isoindolinone (3 g), m.p. 143° C., is obtained.

3-Chloro-2-(7-chloro-1,8-naphthyridin-2-yl)-1-isoindolinone may be prepared as described in Example 6.

EXAMPLE 40

3-Dimethylaminopropylamine (5.1 g) is added at a temperature in the region of 20° C. to a solution of 3-hydroxy-2-(7-methoxy-1,8-naphthyridin-2-yl)-1-isoindolinone (12.4 g) in anhydrous dimethylformamide (200 cc), and the reaction mixture is heated to reflux for 8 hours. After being cooled, the reaction mixture is poured into a mixture of water (1200 cc) and ethyl acetate (500 cc) and filtered to remove an insoluble product. The aqueous phase is separated after settling has occurred and then extracted with ethyl acetate (2×250 cc). The organic phases are combined, washed with water (5×80 cc), dried over magnesium sulphate, filtered and then concentrated to dryness under reduced pressure (2.7 kPa) at 60° C. After recrystallization in ethyl acetate, 3-(3-dimethylaminopropylamino)-2-(7-methoxy-1,8-naphthyridin-2-yl)-1-isoindolinone (5.1 g), m.p. 128° C., is obtained.

3-Hydroxy-2-(7-metoxy-1,8-napthyridin-2-yl)-1-isoindolinone may be prepared by the method described in Belgian Patent 815,019.

EXAMPLE 41

3-Dimethylaminopropanethiol (4.7 g) is added to a solution of mixed 2-(7-methoxy-1,8-naphthyridin-2-yl)-3-oxo-1-isoindolinyl phenyl carbonate (11 g) in acetonitrile (130 cc), and the reaction mixture is heated to reflux for 6 hours. The mixture is then concentrated to dryness under reduced pressure (2.7 kPa) at 60° C. and the residue obtained is dissolved in ethyl acetate (600 cc). The solution obtained is washed with distilled water (4 ×40 cc) and extracted with 1N aqueous hydrochloric acid solution (3×150 cc). The aqueous phases are combined, alkalinized with 5N aqueous sodium hydroxide solution to a pH in the region of 11, and then extracted with ethyl acetate (3×150 cc). The organic phases are combined, washed with water (4×40 cc), dried over magnesium sulphate, filtered and concentrated to dryness under reduced pressure (2.7 kPa). After recrystallization in a mixture of acetonitrile and diisopropyl ether (50:50 by volume), 3-(3-dimethylaminopropylthio)-2-(7-methoxy-1,8-naphthyridin-2-yl)-1-isoindoline (3.8 g), m.p. 113° C., is obtained.

2-(7-Methoxy-1,8-naphthyridin-2-yl)-3-oxo-1-isoindolinyl phenyl carbonate may be prepared in the following manner: phenyl chloroformate (18.8 g) is added at a temperature in the region of 0° C. to a suspension of 3-hydroxy-2-(7-methoxy-1,8-naphthyridin-2-yl)-1-isoindolinone (12.3 g) in anhydrous pyridine (150 cc). The solution obtained is stirred for 1 hour at a temperature in the region of 20° C. and then poured into distilled water (500 cc). The insoluble product formed is separated by filtration and dissolved in dichloromethane (800 cc). The solution obtained is washed with water (3×75 cc), dried over magnesium sulphate, filtered and concentrated to dryness under reduced pressure (2.7 kPa). After recrystallization in acetonitrile, 2-(7-methoxy-1,8-naphthyridin-2-yl)-3-oxo-1-isoindolinyl phenyl carbonate (15.6 g), m.p. 145° C., is obtained.

3-Dimethylamino-1-propanethiol may be prepared by the method described by ANDREWS K. J. M. et al., J. Chem. Soc., (1953), 2998 - 3002.

3-Hydroxy-2-(7-methoxy-1,8-naphthyridin-2-yl)-1-isoindolinone may be prepared by the method described in Belgian Patent 815,019.

EXAMPLE 42

Working as in Example 1, but starting with 5-hydroxy-6-(7-methoxy-1,8-naphthyridin-2-yl)-7-oxo-2,3,6,7-tetrahydro-5H-[1,4]dithiino[2,3-c]pyrrole (1.75 g), sodium hydride (0.15 g) and a 1.5M solution (4 cc) of 1-chloro-3-dimethylaminopropane in toluene, and heating the reaction mixture for 45 minutes at 75° C., 5-(3-dimethylaminopropoxy)-6-(7-methoxy-1,8-naphthyridin-2-yl)-7-oxo--2,3,6,7-tetrahydro-5H-[1,4]dithiino[2,3-c]pyrrole fumarate (0.3 g), m.p. 240° C., is obtained.

5-Hydroxy-6-(7-methoxy-1,8-naphthyridin-2-yl)-7-oxo-2,3,6,7-tetrahydro-5H-[1,4]dithiino[2,3-c]pyrrole may be prepared by the method described in Belgian Patent 808,152.

1-Chloro-3-dimethylaminopropane may be prepared by the method of GRAY A. P. et al., J. Am. Chem. Soc., (1955), 77, 3533.

EXAMPLE 43

The procedure is as in Example 22, but starting with N,N-dimethylglycolamide (4.6 g) in tetrahydrofuran (200cc), an oily suspension (50% by weight; 2.2 g) of sodium hydride and 5-chloro-6-(7-chloro-1,8-naphthyridin-2-yl)-6,7-dihydro-7-oxo-5H-pyrrolo[3,4-b]pyrazine. After recrystallization in dimethylformamide, {6-(7-chloro-1,8-naphthyridin-2-yl)-6,7-dihydro-7-oxo-5H-pyrrolo[3,4b]-pyrazin-5-yloxy}-N,N-dimethylacetamide (2.25 g), m.p. 309° C., is obtained.

5-Chloro-6-(7-chloro-1,8-naphthyridin-2-yl)-6,7-dihydro-7-oxo-5H-pyrrolo[3,4-b]pyrazine is prepared in a manner similar to that described in Example 6 for the preparation of 3-chloro-2-(7-chloro-1,8-naphthyridin-2-yl)-1-isoindolinone, but starting with 5-hydroxy-6-(7-methoxy-1,8-naphthyridin-2-yl)-7-oxo-6,7-dihydro-5H-pyrrolo[3,4-b]pyrazine (23.2 g), sulphinyl chloride (300 cc) and dimethylformamide (1 cc). 5-Chloro-6-(7-chloro-1,8-naphthyridin-2-yl)-7-oxo-6,7-dihydro-5H-pyrrolo[3,4-b]-pyrazine (21 g ) m.p. 264° C., is thereby obtained.

5-Hydroxy-6-(7-methoxy-1,8-naphthyridin-2-yl)-7-oxo-6,7-dihydro-5H-pyrrolo[3,4-b]pyrazine may be prepared by the method described in Belgian Patent 815,019.

3-Dimethylaminopropionic acid hydrochloride may be prepared by the method of CLARK H. T. et al., J. Am. Chem. Soc., 1933, 55, 4571.

EXAMPLE 44

N,N'-Carbonyldiimidazole (1.35 g) is added to a solution of [2-(7-methoxy-1,8-naphthyridin-2-yl)-3-oxo-1-isoindolinyloxy]acetic acid (3 g) in anhydrous dimethylformamide (70 cc), and the mixture is stirred for 2 hours at a temperature in the region of 25° C. Propylamine (0.4 g) is then added and the mixture is stirred again for 16 hours at a temperature in the region of 25° C. The reaction mixture is then poured into water (150 cc) and the precipitate obtained is separated by filtration, washed with water, dried under reduced pressure (0.05 kPa) and recrystallized in ethanol. [2-(7-Methoxy-1,8-naphthyridin-2-yl)-3-oxo-1-isoindolinyloxy]-N-propylacetamide (2.95 g), m.p. 174° C., is thereby obtained.

[2-(7-Methoxy-1,8-naphthyridin-2-yl)-3-oxo-1-isoindolinyloxy]acetic acid may be prepared in the following manner: a solution of tert-butyl [2-(7-methoxy-1,8-naphthyridin-2-yl)-1-isoindolinyloxy]acetate (29.4 g) in trifluoroacetic acid is stirred for 2 hours at a temperature in the region of 25° C. The reaction mixture is then concentrated to dryness and the residue obtained is stirred in isopropyl ether (200 cc). The crystallized solid obtained is separated by filtration and then taken up with water (400 cc). The mixture is brought to pH 10 with 4N aqueous sodium hydroxide solution. An insoluble product is separated by filtration; the filtrate is washed with ethyl acetate (3×200 cc) and then acidified to pH 2 with 4N aqueous hydrochloric acid solution. The precipitate obtained is separated by filtration, washed with water and dried in the air. [2-(7-Methoxy- 1,8-naph-thyridin-2-yl)-1-isoindolinyloxy]acetic acid (14.6 g), m.p. 190° C., is thereby obtained.

Tert-butyl [2-(7-methoxy-1,8-naphthyridin-2-yl)-3-oxo-1-isoindolinyloxy]acetate may be prepared in the following manner: an oily suspension (50% by weight; 7.2 g) of sodium hydride is added in the course of 15 minutes to a suspension, maintained at a temperature in the reregion of 0° C., of 3-hydroxy-2-(7-methoxy-1,8-naphthythyridin-2-yl)-1-isoindolinone (46 g) in dimethylformamide (600 cc), and the mixture is stirred for 1 hour 30 minutes at this temperature. A solution of tert-butylbromacetate (32.1 g) in dimethylformamide (100 cc) is then added in the course of 10 minutes, and the mixture is stirred for 2 hours at 60° C. The insoluble product formed is separated by filtration. The filtrate is poured into water (300 cc) and the insoluble product obtained is separated by filtration, washed and dried in the air. Tert-butyl [2-(7-methoxy-1,8-naphthyridin-2-yl)-3-oxo-1isoindolinyloxy]-acetate (32.6 g), m.p. 188° C., is thereby obtained.

EXAMPLE 45

The procedure is as in Example 44, but starting with [2-(7-methoxy-1,8-naphthyridin-2-yl)-3-oxo-1-isoindolinyloxy]acetic acid (4.5 g) in anhydrous dimethylformamide (100 cc), N,N'-carbonyldiimidazole (2 g) and butylamine (0.73 g). After recrystallization in acetonitrile, [2-(7-methoxy-1,8-naphthyridin-2-yl)-3-oxo-1-isoindolinyloxy]-N-butylacetamide (2.35 g), m.p. 170° C., is obtained.

EXAMPLE 46

N,N'-Carbonyldiimidazole (1.8 g) is added at a temperature in the region of 25° C. to a solution of [2-(7-methoxy-1,8-naphthyridin-2-yl)-3-oxo-1-isoindolinyloxy]acetic acid (4 g) in anhydrous dimethylformamide (85 cc), and the mixture is stirred for 2 hours at this temperature. 2-Dimethylaminoethylamine (0.7 g) is then added and the mixture is stirred for 18 hours at this same temperature. The reaction mixture is then poured into water (200 cc) and extracted with methylene chloride (3×200 cc). The organic extracts are washed with water, dried and concentrated to dryness under reduced pressure (2.7 kPa) at 40° C. The residue obtained is crystallized by stirring in ethyl ether. [2-(7-Methoxy-1,8-naphthyridin-2-yl)-3-oxo-1-isoindolinyloxy]-N-(2-dimethylamino ethyl)acetamide (3.5 g), m.p. 146° C., is thereby obtained.

EXAMPLE 47

The procedure is as in Example 44, but starting with [2-(7-methoxy-1,8-naphthyridin-2-yl)-3-oxo-1-isoindolinyloxy]acetic acid (3.5 g) in anhydrous dimethylformamide (80 cc), N;N'-carbonyldiimidazole (1.6 g) and 2-methoxyethylamine (0.65 g). After recrystallization in ethanol, [2-(7-methoxy-1,8-naphthyridin-2-yl)-3-oxo-1isoindolinyloxy]-N-(2-methoxyethyl)acetamide (3 g), m.p. 172° C., is obtained.

EXAMPLE 48

The procedure is as in Example 44, but starting with [2-(7-methoxy-1,8-naphthyridin-2-yl)-3-oxo-1-isoindolinyloxy]acetic acid (3 g) in anhydrous dimethylformamide (65 cc), N,N'-carbonyldiimidazole (1.35 g) and 1,4-dioxa-8-azaspiro[4.5]decane (1 g). After two successive recrystallizations in carbon tetrachloride and isopropyl ether, 2-(7-methoxy-1,8-naphthyridin-2-yl)-3-[2-(4-ethylenedioxypiperidino)-2-oxoethoxy]-1-isoindolinone (2.8 g), m.p. 137° C., is obtained.

EXAMPLE 49

The procedure is as in Example 44, but starting with [2-(7-methoxy-1,8-naphthyridin-2-yl)-3-oxo-1-isoindolinyloxy]acetic acid (3.1 g) in anhydrous dimethylformamide (70 cc), N,'-carbonyldiimidazole (1.4 g) and N-methylpropylamine (0.6 g). After recrystallization in ethanol, [2-(7-methoxy-1,8-naphthyridin-2yl)-3-oxo1-isoindolinyloxy]-N-methyl-N-propylacetamide (2.7 g), m.p. 160° C., is obtained.

EXAMPLE 50

The procedure is as in Example 44, but starting with [2-(7-methoxy-1,8-naphthyridin-2-yl)-3-oxo-1-isoindolinyloxy]acetic acid (3 g) in anhydrous dimethylformamide (65 cc), N,'-carbonyldiimidazole (1.3 g) and 3-methylbutylamine (0.61 g). After recrystallization in ethanol, [2-(7-methoxy-1,8-naphthyridin-2-yl)-3-oxo-1isoindolinyloxy]-N-(3-methylbutyl)acetamide (2.45 g), m.p. 136° C., is obtained.

EXAMPLE 51

The procedure is as in Example 22, but starting with 1-(2-hydroxyethyl)-4-acetylpiperazine (7.75 g) in anhydrous tetrahydrofuran (250 cc), an oily suspension (50% by weight; 2.3 g) of sodium hydride and 3-chloro-2(-7-chloro-1,8-naphthyridin-2-yl)-1-isoindolinone (10 g). After crystallization successively in 2-propanol and then in ethanol, 3-[2-(4-acetyl-1-piperazinyl)ethoxy]-2-(7-chloro-1,8-naphthyridin-2-yl)-1-isoindolinone (4.3 g), m.p. 172° C., is obtained.

1-(2-Hydroxyethyl)-4-acetylpiperazine may be prepared according to the method described by HALL H. K., J. Am. Chem. Soc., 78, 2570 (1956).

EXAMPLE 52

The procedure is as in Example 44, but starting with [2-(7-methoxy-1,8-napthyridin-2-yl)-3-oxo-1-isoindolinyloxy] acetic acid (3.5 g) in anhydrous dimethylformamide (70 cc), N,'-carbonyldiimidazole (1.6 g) and 4-hydroxypiperidine (0.82 g). After recrystallization in ethanol, 3-[2-(4-hydroxy-1-piperidyl)-2-oxoethoxy]-2-(7-methoxy-1,8-naphthyridin-2-yl)-1-isoindolinone (3.7 g), m.p. 167° C., is obtained.

EXAMPLE 53

The procedure is as in Example 7, but starting with 4-acetylaminobutanol (6 g) in anhydrous tetrahydrofuran (250 cc), an oily suspension (50% by weight; 2.3 g) of sodium hydride and 3-chloro-2-(7-chloro-1,8-naphthyridin-2-yl)-1-isoindolinone (10 g). The product obtained is purified by chromatography on neutral alumina (40 g) contained in a column 1.5 cm in diameter, and eluting with methylene chloride and collecting 10-cc fractions. Fractions 3 to 50 are combined and concentrated to dryness under reduced pressure (2.7 kPa) at 40° C., and the residue obtained is crystallized by stirring into 2-propanol. 3-(4-Acetylaminobutoxy)-2-(7-chloro-1,8-naphthyridin-2-yl)-1-isoindolinone (0.8 g), m.p. 120° C., is thereby obtained.

4-Acetylaminobutanol may be prepared in the following manner: a solution of phenyl acetate (34 g) in acetonitrile (50 cc) is added in the course of 45 minutes at a temperature in the region of 25° C. to a solution of 4-amino-1-butanol (22.3 g) in acetonitrile (75 cc), and the mixture is then heated to reflux for 2 hours. The reaction mixture is then concentrated to dryness under reduced pressure (2.7 kPa at 40° C., and then 0.1 kPa at 75° C.). 4-Acetylaminobutanol (29.3 g) is thereby obtained in the form of an oil, which is employed in the crude state in the subsequent syntheses.

EXAMPLE 54

The procedure is as in Example 26, but starting with 3-hydroxy-2-(7-methyl-1,8-naphthyridin-2-yl)-1-isoindolinone (7.3 g) in anhydrous dimethylformamide (200 cc) and using an oily suspension (50% by weight; 1.8 g) of sodium hydride and N-propyl-chloroacetamide (5.1 g). After crystallization of the product from petroleum ether, [2-(7-methyl-1,8-naphthyridin-2-yl)-3-oxo-1-isoindolinyl]-N-propylglycolamide (1.5 g), m.p.128-130° C., is obtained.

EXAMPLE 55

Working as in Example 22, but starting with 1-butanol (5.8cc) in anhydrous dimethylformamide (625 cc), an oily suspension (50% by weight; 3.1 g) of sodium hydride and 3-chloro-2-(7-chloro-1,8-naphthyridin-2-yl)-1-isoindolinone (20.7 g), 3-butoxy-2-(7-chloro-1,8-naph-thyridin-2-yl)-1-isoindolinone (5.6 g), m.p. 128° C., is obtained after recrystallization in isopropyl ether.

EXAMPLE 56

The procedure is as in Example 26, but starting with 2-(7-bromo-1,8-naphthyridin-2-yl)-3-hydroxy-1-isoindolinone (12 g) in anhydrous dimethylformamide (300 cc), an oily suspension (50% by weight; 2.4 g) of sodium hydride and N-(propyl)chloroacetamide (6.9 g). After recrystallization in acetonitrile, [2-(7-bromo-1,8-naphthyridin-2-yl)-3-oxo-1-isoindolinyl]-N-propylglycolamide (2.1 g), m.p. 174° C., is obtained.

2-(7-Bromo-1,8-naphthyridin-2-yl)-3-hydroxy-1-isoindolinone may be prepared as described in Belgian Patent No. 815,019.

EXAMPLE 57

An oily suspension (50% by weight; 0.96 g) of sodium hydride is added in the course of 15 minutes to a suspension of 3-hydroxy-2-(7l-methoxy-1,8-naphthyridin- 2-yl)-1-isoindolinone (6.15 g) in anhydrous dimethylformahide (50 cc) while the temperature is maintained in the region of 0° C. The mixture is stirred for a further 30 minutes at this temperature, and there is then added, in the course of 1 hour, diethyl chlorophosphate (2.9 cc) followed by a solution of sodium 4-methylpentylate, which is prepared from 4-methylpentanol (2.45 g) in anhydrous dimethylformamide (30 cc) and an oily suspension (50% by weight; 0.96 g) of sodium hydride. The mixture is then stirred for 20 hours at a temperature in the region of 20° C. and then poured into water (400 cc). The product is extracted with methylene chloride (3×200 cc) and the organic phases are combined, washed with water, dried and concentrated to dryness under reduced pressure (2.7 kPa) at 40° C. The residue obtained is purified by chromatography on silica (0.063–0.2 mm; 250 g) contained in a column 4 cm in diameter [eluant: ethyl acetate/cyclohexane (1:1 by volume)], collecting 50-cc fractions. Fractions 22 to 43 are combined and concentrated to dryness under reduced pressure (0.15 kPa). After recrystallization of the residue from a mixture of isopropyl ether and ethyl ether (50:50 by volume), 2-(7-methoxy-1,8-naphthyridin-2-yl)-3-(4-methylpentyloxy)-1-isoindolinone (1.8 9), m.p. 88° C., is obtained.

EXAMPLE 58

Triethylamine (2 cc) and 4-methylpentylamine (2 g) are added to a suspension, maintained under an argon atmosphere, of 3-chloro-2-(7-chloro-1,8-naphthyridin-2-yl)-1-isoindolinone (5 g) in anhydrous dimethylformamide (50 cc). The reaction mixture is stirred for 1 hour 30 minutes at a temperature in the region of 20° C. and then heated with stirring to a temperature of 60° C. for 3 hours. After being cooled, the mixture is poured into ice (100 g) and water (300 cc) and then extracted with dichloromethane (2×200 cc). The organic phases are combined, washed with water (4×50 cc), dried over magnesium sulphate, filtered and concentrated to dryness under reduced pressure (2.7 kPa) at 40° C. Ethyl acetate (300 cc) is added to the residue obtained. An insoluble product is removed by filtration and the filtrate is concentrated to dryness under reduced pressure (2.7 kPa) at 40° C. The residue obtained is crystallized successively in ethyl acetate and acetonitrile. 2-(7-Chloro-1,8-naphthyridin-2-yl)-3-(4-methylpentylamino)-1-isoindolinone (1.4 g), m.p. 131° C., is thereby obtained.

4-Methylpentylamine may be prepared by the method described by SHAPIRO S. L. et al., J. Am. Chem. Soc., (1959), 81, 3728.

The present invention also provides pharmaceutical compositions which contain a pyrrole derivative of formula (I) in combination with an adjuvant, a diluant and/or a coating which is compatible and pharmaceutically acceptable. These medicinal products may be used orally, rectally, parenterally or percutaneously.

As solid compositions for oral administration, tablets, pills, powders (generally in gelatin capsules) or granules may be used. In these compositions, the active product according to the invention is mixed with one or more inert diluants such as succrose, lactose or starch. These compositions can also contain substances other than diluants, e.g. a lubricant such as magnesium stearate.

As liquid compositions for oral administration, emulsions that are pharmaceutically acceptable, solutions, suspensions, syrups and elixirs containing inert diluants, such as water or liquid paraffin, may be used. These compositions can also contain substances other than diluants, e.g. wetting, sweetening or flavouring products.

The compositions according to the invention for parenteral administration can be suspensions, emulsions or aqueous or non-aqueous sterile solutions. As a solvent or vehicle, it is possible to use propylene glycol, a polyethylene glycol, vegetable oils, especially olive oil, or injectable organic esters, e.g. ethyl oleate. These compositions can also contain adjuvants, especially wetting agents, emulsifiers and dispersants. The sterilization may be carried out in several ways, for example using a bacteriological filter, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories which can contain, in addition to the active product, excipients such as cocoabutter or suppo-wax.

The compositions for percutaneous administration are creams, ointments, lotions and linaments, in which the active product is combined with liquid or pasty excipients, preferably in combination with a vehicle which promotes percutaneous migration.

The medicinal products and compositions according to the invention are especially useful in human therapy on account of their anxiolytic, hypnotic, anticonvulsant, antiepileptic and muscle relaxant action.

In human therapy, the doses depend on the effect sought and the period of treatment; they are generally between 10 and 500 mg per day orally for an adult.

In general, the doctor will determine the dosage which he considers most suitable in relation to the age and weight and all other factors particular to the subject to be treated.

The examples which follow illustrate a composition according to the invention.

EXAMPLE A

Tablets containing 10-mg doses of active product and having the following composition are prepared according to the usual technique:

| | |
|---|---|
| 2-(7-Chloro-1,8-naphthyridin-2-yl)-3-(3-dimethylaminopropoxy)-1-isoindolinone | 0.011 g |
| Starch | 0.200 g |
| Precipitated silica | 0.035 g |
| Magnesium stearate | 0.004 g |

Working in the same manner, tablets may be prepared in which the active principle consists of the following products:
[2-(7-chloro-1,8-naphthyridin-2-yl)-3-oxo-1-isoindolinyloxy]-N-(2-methylpropyl)acetamide
[2-(7-chloro-1,8-naphthyridin-2-yl)-3-oxo-1-isoindolinyloxy]-N-propylacetamide
2-(7-chloro-1,8-naphthyridin-2-yl)-3-[2-(4-methyl-1-piperazinyl)-2-oxoethoxy]-1-isoindolinone
[2-(7-chloro-1,8-naphthyridin-2-yl)-3-oxo-1-isoindolinyloxy]-N,N-pentamethyleneacetamide
2-(7-chloro-1,8-naphthyridin-2-yl)-3-(5-methylhexyloxy)-1-isoindolinone
[2-(7-chloro-1,8-naphthyridin-2-yl)-3-oxo-1-isoindolinyloxy]-N-isopropylacetamide
[2-(7-methoxy-1,8-naphthyridin-2-yl)-3-oxo-1-isoindolinyloxy]-N-butylacetamide.

We claim:

1. A pyrrole derivative of the formula:

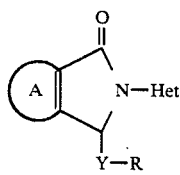

in which A forms with the pyrrole ring an isoindoline ring-system, Y denotes an oxygen or sulphur atom or an imino radical, Het denotes a naphthyridinyl which is unsubstituted or substituted by halogen, (1 to 4 C) alkyl, (1 to 4 C) alkyloxy, (1 to 4 C) alkylthio, cyano or trifluoromethyl and R denotes straight- or branched-chain alkenyl of 3 to 10 carbon atoms or alkyl which is unsubstituted or substituted by alkyloxy, alkylthio, cycloalkyl, alkylcarbonyl, cycloalkylcarbonyl, in which the cycloalkyl has 3 to 6 carbon atoms, cycloalkylcarbamoyl in which the cycloalkyl portion has 3 to 6 carbon atoms, amino, alkylamino, dialkylamino, alkylcarbonylamino, carbamoyl, alkylcarbamoyl, dialkylcarbamoyl, aminoalkylcarbamoyl, alkylaminoalkylcarbamoyl, dialkylaminoalkylcarbamoyl, alkyloxyalkylcarbamoyl, or phenyl, the aforesaid alkyl radicals being straight- or branched-chain radicals and containing, except where specifically stated, 1 to 10 carbon atoms each, and, when they exist, its pharmaceutically acceptable salt and optical isomers.

2. A pyrrole derivative according to claim 1 in which A forms with the pyrrole ring an isoindoline, Y denotes an oxygen or sulphur atom or an imino radical, Het denotes a 1,8-naphthyridin-2-yl radical substituted by halogen, (1 to 4 C) alkyl or (1 to 4 C) alkyloxy, and R denotes straight- or branched chain alkenyl of 3 to 10 carbon atoms or alkyl which is unsubstituted or substituted by alkyloxy, cycloalkyl, alkylcarbonyl, cycloalkylcarbonyl in which the cycloalkyl has 3 to 6 carbon atoms, cycloalkylcarbamoyl in which the cycloalkyl portion has 3 to 6 carbon atoms, dialkylamino, alkylcarbonylamino, alkylcarbamoyl, dialkylcarbamoyl, dialkylaminoalkylcarbamoyl, or alkyloxyalkylcarbamoyl radical, the said alkyl radicals having, except where specifically stated, 1 to 6 carbon atoms each in a straight- or branched-chain.

3. A pyrrole derivative according to claim 1 in which A forms with the pyrrole ring, an isoindoline ring-system, Y denotes an oxygen atom, Het denotes a 1,8-naphthyridin-2-yl radical substituted by halogen, (1 to 4 C.) aklyl, or (1 to 4 C) alkyloxy and R denotes alkyl which is unsubstituted or substituted by alkyloxy, cycloalkyl of 3 to 6 carbon atoms, alkylcarbonyl, cycloalkylcarbamoyl radical in which the cycloalkyl has 3 to 6 carbon atoms, dialkylamino, alkylcarbamoyl, or dialkylcarbamoyl, the said alkyl radicals being straight-or branched-chain radicals and containing, except where specifically stated, 1 to 10 carbon atoms each.

4. A pyrrole derivative according to claim 1 which is [2-7-chloro-1,8-napthyridin-2-yl)-3-oxo-1-isoindolinyloxy]-N-(2-methylpropyl)acetamide.

5. A pyrrole derivative according to claim 1 which is [-(7chloro-1,8-naphthyridin-2-yl)-3-oxo-1-isoindolinyloxy-N-propylacetamide.

6. A pyrrole derivative according to claim 1 which is [2-chloro-1,8-naphthyridin-2yl)-3-oxy-1-isoindolinyloxy]-N,N-pentamethyleneacetamide.

7. A pyrrole derivative according to claim 1 which is 2-(7-chloro-1,8-naphthyridin-2-yl)-3-(5-methylhexyloxy)-1-isoindolinone.

8. A pyrrole derivative according to claim 1 which is [2-(7-chloro-1,8-naphthyridin-2-yl)-3-oxy-1-isoindolinyloxy]-N-isopropylacetamide.

9. A pyrrole derivative according to claim 1 which is [2-(7-methoxy-1,8-naphthyridin-2yl)-3oxo-1-isoindolinyloxy -N-butylacetamide.

10. A pharmaceutical composition useful as an anxiolytic, hypnotic, anticonvulsant, anti-epileptic or muscle relaxant, which contains, in combination with one or more diluants or adjuvants that are compatible and pharmaceutically acceptable, an effective amount of at least one pyrrole derivative of the formula:

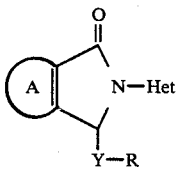 (I)

in which A forms with the pyrrole ring an isoindoline ring-system, Y denotes an oxygen or sulphur atom or an amino radical, Het denotes a naphthyridinyl radical which is unsubstituted or substituted by halogen, (1 to 4 C) alkyl, (1 to 4 C) alkyloxy, (1 to 4C) alkylthio, cyano or trifluoromethyl and R denotes straight- or branched-chain alkenyl of 3 to 10 carbon atoms or alkyl which is unsubstituted or substituted by alkyloxy, alkylthio, cycloalkyl, alkylcarbonyl, cycloalkylcarbonyl, in which the cycloalkyl has 3 to 6 carbon atoms, cycloalkylcarbamoyl in which the cycloalkyl portion has 3 to 6 carbon atoms, amino, alkylamino, dialkylamino, alkylcarbonylamino, carbamoyl, alkylcarbamoyl, dialkylcarbamoyl, aminoalkylcarbamoyl, alkylaminoalkylcarbamoyl, dialkylaminoalkylcarbamoyl, alkyloxyalkylcarbamoyl, or phenyl, the aforesaid alkyl radicals being straight- or branched-chain radicals and containing, except where specifically stated, 1 to 10 carbon atoms each, and, when they exist, its pharmaceutically acceptable salt and optical isomers.

11. A method of producing an anxiolytic, hypnotic, anticonvulsant, antiepileptic or muscle relaxant therapeutic effect in a subject in whom such therapy is desired which comprises administering to such a subject an effective amount of a pyrrole derivative as claimed in claim 1.

* * * * *

UNITED STATES PATENT AND TRADEMARK OFFICE
CERTIFICATE OF CORRECTION

PATENT NO. : 4,898,871
DATED : February 6, 1990
INVENTOR(S) : BOURZAT et al.

It is certified that error appears in the above-identified patent and that said Letters Patent is hereby corrected as shown below:

column 6, line 39: read "ring-system"

column 8, line 56: read "2-chloroacetamide"

column 18, line 46: read "oxo-1-isoindolinyloxy"

column 24, lines 8 and 18: read "N,N'-carbonyldiimidazole"

column 27, line 32: read "N-(2-methylpropyl..."

column 28, lines 42 and 46: read "[2-(7-chloro...".

Signed and Sealed this

Nineteenth Day of March, 1991

*Attest:*

HARRY F. MANBECK, JR.

*Attesting Officer*     *Commissioner of Patents and Trademarks*